United States Patent

Le Bras-Roulier et al.

[11] Patent Number: 5,948,395
[45] Date of Patent: Sep. 7, 1999

[54] ANHYDROUS COSMETIC COMPOSITION IN THE FORM OF A SOFT PASTE AND PROCESS FOR THE PREPARATION THEREOF

[75] Inventors: Véronique Le Bras-Roulier, Paris; Dolorès Miguel-Colombel, La Reine, both of France

[73] Assignee: L'Oreal, Paris, France

[21] Appl. No.: 09/070,848

[22] Filed: May 1, 1998

Related U.S. Application Data

[63] Continuation of application No. 08/539,160, Oct. 4, 1995.

[30] Foreign Application Priority Data

Jun. 10, 1994 [FR] France .................................. 94 11946

[51] Int. Cl.$^6$ ............................ A61K 7/025; A61K 7/00; A61K 7/02; A61K 7/48
[52] U.S. Cl. ................................ 424/64; 424/63; 514/844
[58] Field of Search ........................... 424/63, 64, 70.12, 424/401; 514/844

[56] References Cited

U.S. PATENT DOCUMENTS

| | | |
|---|---|---|
| 4,578,266 | 3/1986 | Tietjen . |
| 5,085,855 | 2/1992 | Shore . |
| 5,118,507 | 6/1992 | Clement . |
| 5,288,482 | 2/1994 | Krzysik . |
| 5,306,488 | 4/1994 | Vanlerberghe et al. . |
| 5,750,120 | 5/1998 | Miguel-Colombel .................... 424/401 |

FOREIGN PATENT DOCUMENTS

602905  12/1993  European Pat. Off. .

*Primary Examiner*—Robert H. Harrison
*Attorney, Agent, or Firm*—Finnegan, Henderson, Farabow, Garrett & Dunner, L.L.P.

[57] ABSTRACT

An anhydrous cosmetic composition in the form of a soft paste, which comprises silicone materials, particularly a silicone gum, and a at least one wax. A process of preparation of such a material, involving mixing, heating, cooling, and kneading steps.

27 Claims, No Drawings

ANHYDROUS COSMETIC COMPOSITION IN THE FORM OF A SOFT PASTE AND PROCESS FOR THE PREPARATION THEREOF

This application is a continuation of Ser. No. 08/539,160 filed Oct. 4, 1995.

The invention relates to a composition, for example a cosmetic or pharmaceutical composition, which is provided in the form of a soft paste and can be used for making up, in particular the lips, or as a base for the treatment of the skin and/or lips.

The cosmetic compositions which can be applied to the lips as a make-up or care product generally contain fatty substances and waxes, and optionally additives and pigments.

It is known that the consistency of the composition becomes firmer as the amount of waxes present in the composition increases, which enables it to be used in the form of a stick.

Presentation of a product, in particular a lip color composition in the form of a stick has some disadvantages. For example, the drawing of the outlines of the lips is difficult, and the resistance of the stick to heat is not optimum.

To obtain a cosmetic composition with a softer texture, there have been proposals to introduce gums into the formulation, which make it possible to confer significant qualities of softness and ease of spread on the final composition, while preventing the composition from being oily. Among the gums which can be incorporated in these compositions, silicone gums have proved to be particularly advantageous in making it possible to obtain the desired texture.

Introduction of silicone gums, however, into a composition which is rich in fatty substances, such as a lipstick, presents a problem.

In fact, when a mixture is prepared comprising fatty substances, such as are commonly used in the cosmetics industry, and silicone gums, the appearance of two phases is generally observed. These two phases result from the fact that the silicone gums cannot be homogeneously mixed with fatty substances when the techniques of the prior art are used.

To overcome this disadvantage, a number of solutions can be envisaged, among which there may be mentioned:

- dissolving the silicone gums beforehand in a solubilizing oil with a low boiling point, such as a silicone oil; however, this solution is not satisfactory because storage problems can arise, in particular due to the evaporation of the volatile silicones.
- the exclusive use of silicone fatty substances; this solution certainly makes it possible to obtain a homogeneous mixture but the introduction of a non-silicone fatty substance inevitably results in phase separation.
- the use of short esters such as isopropyl myristate, a fatty substance compatible both with the silicone products and the non-silicone fatty substances; however, the use of this ester can result in a certain sensitization of the mucous membrane.

The aim of the present invention is to overcome the disadvantages of the prior art and to provide a process which makes it possible to obtain a stable, homogeneous and anhydrous cosmetic composition comprising silicone gums and silicone fatty substances and/or non-silicone fatty substances.

A subject of the present invention is therefore a composition comprising at least one silicone gum and at least one fatty substance, the fatty substance including at least one wax, wherein the composition is anhydrous and in the form of a soft paste, and further wherein said composition is suitable for topical use. Preferably, the composition is suitable for topical use. Preferable, the composition of the invention does not contain a gelling agent.

Another subject of the invention is a process for the preparation of an anhydrous composition which is provided in the form of a soft paste and which comprises a silicone gum and fatty substances, including at least one wax, in which:

- at least a portion of the various constituents of the composition, including the wax, is brought to a temperature at which the wax melts;
- the remainder of the constituents, if appropriate, is added; and
- then the mixture obtained is kneaded during at least a part of a cooling step.

The process according to the invention makes it possible to obtain cosmetic compositions comprising silicone or non-silicone fatty substances and silicone gums which are highly homogeneous, without requiring the incorporation of a specific compound for keeping the said compositions stable.

The present invention therefore has the advantage of making it possible to vary the formulations of the compositions without being constrained by the mandatory presence of a certain type of compounds, while obtaining compositions which remain homogeneous and stable over time.

Surprisingly, the compositions according to the invention have an original and novel soft texture and exhibit, after application, good hold and high gloss.

In the continuation of the present description, the percentages are give by weight, except when otherwise indicated.

The composition according to the present invention therefore comprises at least one siliconed gum and at least one fatty substance, including at least one wax.

The silicone gum can generally be present in an amount by weight of the order of 0.1–10%, preferably from 0.1 to 5%, and more preferably from 0.1 to 3% with respect to the weight of the final composition.

Use is preferably made, alone or as a mixture, of a silicone gum having a molecular weight of less than 1,500,000, such as a polydimethylsiloxane, a polyphenylsiloxane or a ployhydroxysiloxane. The preferred range of molecular weight for the silicone gum is from 200,000 to 1,500,000.

In particular, use may be made of a silicone gum corresponding to the formula:

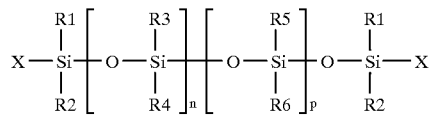

in which:

- $R_1$, $R_2$, $R_5$ and $R_6$ each independently represents as alkyl radical having from 1 to 6 carbon atoms,
- $R_3$ and $R_4$ each independently represents an alkyl radical having from 1 to 6 carbon atoms or an aryl radical,
- X is an alkyl radical having from 1 to 6 carbon atoms, a hydroxyl radical or a vinyl radical, and
- n and p are chosen to give the silicone gum a viscosity greater than 100,000 mPa.s, preferably greater than 500,000 mPa.s.

Generally, n and p can take values from 0 to 5000, preferably from 0 to 3000.

The silicone gum can be introduced into the composition as such or in a diluted form in a silicone oil, such as a PDMS (polydimethylisoxane).

Mention may be made, as a silicone gum which can be used according to the invention, of those in which:

- the substituents $R_1$ to $R_6$ and X represent a methyl group, p=0 and n=2,700, like that sold under the name SE30 by the company General Electric,
- the substituents $R_1$ to $R_6$ and X represent a methyl group, p=0 and n=2300, like that sold under the name AK 500000 by the company Wacker,
- the substituents $R_1$ to $R_6$ represent a methyl group, the substituent X represents a hydroxyl group, p=0 and n=2700, as a 13% solution in cyclopentasiloxane, like that sold under the name Q2-1401 by the company Dow Corning,
- the substituents $R_1$ to $R_6$ represent a methyl group, the substituent X represents a hydroxyl group, p=0 and n=2700, as a 13% solution in dimethicone, like that sold under the name Q2-1403 by the company Dow Corning,
- the substituents $R_1$, $R_2$, $R_5$, $R_6$ and X represent a methyl group and the substituents $R_3$ and $R_4$ represent an aryl group, and p and n are such that the molecular weight of the compound is 600,000, like that sold under the name 761 by the company Rhône-Poulenc.

The composition according to the invention also comprises fatty substances, including at least one wax. In a specific form of the invention, at least a portion of the fatty substances is composed of non-silicone fatty substances.

It is understood that compounds in the form of waxes, oils or pastes from vegetables, animals, minerals, silicones, or synthetic preparation, can be used as fatty substances.

Mention may be made, among the waxes capable of begin used as non-silicone fatty substances, of animal waxes, suchas as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

Mention may be made, among the silicone waxes, of polymethylsiloxane alkyls, alkoxys and/or esters.

The waxes are preferably present in a n amount by weight of 2–50%, preferably 10–30%, with respect to the weight of the final composition.

Mention may be made, among the optional other non-silicone fatty substances, of mineral oils, such as liquid paraffin or liquid petroleum, of animal oils, such as perhydrosqualene or arara oil, or alternatively of vegatable oils, such as sweet almond, calophyllum, palm, castor, avocado, jojaba, olive or cereal germ oil.

It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols.

It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

A pulverulent colouring agent, such as carbon black, chromium or iron oxides, ultramarines, manganese pyrophosphate, iron blue, and titanium dioxide, pearlescent agents, generally used as a mixture with coloured pigments, or some organic dyes, generally used as a mixture with coloured pigments and commonly used in the cosmetics industry, can be added to the composition. In general, these coulouring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8–22 carbon atoms, non-expanded synthetic polymer powders, expanded powders and powders from natural organic compounds, such as cereal starches, which may or may not be crosslinked.

It is additonally possible to incorporate in the said composition any additive commonly used in the cosmetics industry, such as antioxidants, fragrances or preservatives, and cosmetic and/or pharmaceutical active principles, such as vitamin derivatives, essential fatty acids, ceramides or fat-soluble sunscreens, for example.

In order to prepare the composition according to the invention, a premix is first of all prepared comprising at least a portion of the various constituents of the composition, including at least the wax or waxes. This premix is heated to a temperature at which the wax melts. The remainder of the constituents, if appropriate, is added, and the mixture obtained is then kneaded during at least a part of its cooling to room temperature.

This process makes it possible to obtain a composition which exists in the form of a homogeneous and soft paste, although it contains fatty substances and a silicone gum.

More specifically, the invention relates to a process for preparing a cosmetic composition comprising the steps of:

(A) mixing at least one fatty substance, the fatty substance including at least one wax, with at least a portion of components, other than the at least one wax, for the cosmetic composition, the portion optionally including at least one silicone gum (in other words, a mixture is prepared comprising all of the at least one wax and at least a portion of the other various components of the final composition, but the at least one silicone gum is not necessarily added to this mixture);

(B) heating the mixture to a temperature at which the wax melts;

(C) if only a portion of the other components of the composition were mixed in step (A), adding to the mixture after the melting temperature of the wax is obtained but entirely before the cooling step (D), before and during the cooling step (D), or entirely during the cooling step (D), the remainder of the other components, including, if either no silicone gum was added in step (A), or only a portion of the silicone gum was added in step (A), at least one silicone gum to form a mixture containing all components of the cosmetic composition (in other words, if all components, other than the at least one wax, of the ultimate cosmetic composition to be prepared were not added in step (A), the remainder is added either all in step (C), or partly in step (C) and partly in step (D), or all in step (D)). For example, the addition of the remaining components can be made in one step either before or during cooling or in several steps which can occur entirely before cooling, or entirely during cooling, or partly before cooling and party during cooling.

(D) thereafter cooling the mixture (in other words, the mixture containing all the components of the cosmetic composition to be prepared is cooled); and kneading the mixture during at least a part of the cooling step;

whereby a composition is obtained comprising at least one silicone gum and at least one fatty substance, the fatty substance including at least one wax, and further wherein the composition is anhydrous and in the form of a soft paste.

The heating operation can be carried out according to any known technique.

The kneading operation can be carried out by virtue of vigorous stirring or by extrusion by means well-known in the art.

In a specific embodiment of the invention, the heating and kneading operations, indeed even the cooling operation, are carried out in one or a number of extruders arranged one after the other and preferably in a single twin-screw extruder. As is well-known, such twin-screw extruders are readily accessible.

The composition of the invention obtained after extrusion has a specific softness and provides a certain feeling of ease of spread when it is applied to the skin, while avoiding the appearance and the feeling of an oily fat.

The conditions under which the extrusion can be carried out are described in patent application FR94-00726, the contents of which are specifically incorporated by reference herein.

An anhydrous composition for topical use is thus obtained, which composition can be applied to the skin and/or to the lips as a make-up product, for example a lip color composition, and/or a care product.

Depending on the use envisaged, the composition can additionally comprise the constituents commonly used by a person skilled in the art.

The invention is illustrated in more detail in the following examples. These examples in no way limit the scope of the invention.

EXAMPLE 1

A lip-treatment base is prepared which has the following formulation:

| | |
|---|---|
| liquid petrolatum | 22% |
| lanolin | 23% |
| isopropyl lanolate | 23% |
| microcrystalline wax | 15% |
| carnauba wax | 10% |
| butylated hydroxytoluene | 0.2% |
| tocopherol acetate | 1.8% |
| dimethiconol as a 13% solution in dimethicone (Q2-1403 from Dow Corning) | 5% |

These various ingredients are mixed at approximately 100° C., and the mixture is introduced into a twin-screw extruder.

The extrusion is carried out under the following conditions:

| | |
|---|---|
| inlet temperature: | 100° C. |
| outlet temperature: | 30° C. |

-continued

| | |
|---|---|
| residence time: | approximately 3 minutes |
| speed of the screws: | 350 rev/min |

At the outlet, a soft paste is obtained with a viscosity equal to 15 Pa.s, which exists in the form of a single, stable and homogeneous phase and which can be removed and applied using a brush.

After application, this treatment base is regarded as having satisfactory qualities of softness and of ease of spread and does not have an oily texture.

EXAMPLE 2

A lip color composition is prepared which has the following formulation:

| | |
|---|---|
| jojoba oil | 11% |
| castor oil | 25% |
| lanolin | 10% |
| beeswax | 15% |
| polyethylene wax | 17% |
| polybutylene | 4% |
| pigment D&C Yellow No. 6 (CI 15985) | 1% |
| pigment D&C Red No. 27 (CI 45410) | 9% |
| titanium dioxide (CI 77891) | 3% |
| polyphenylsiloxane (Silbione 71634 from Rhone-Poulenc) | 5% |

The pigments are milled in the fatty constituents (oils and lanolin), the other constituents are then added and the mixture is heated to 100° C. The preparation is continued in a way similar to that in Example 1, and a lip color composition is obtained with a viscosity equal to 16 Pa.s and which has satisfactory qualities of softness and ease of spread.

EXAMPLE 3

A lip color composition is prepared with the following formulation:

| | |
|---|---|
| jojoba oil | 20% |
| liquid petrolatum | 20% |
| lanolin | 21% |
| talc | 5% |
| nylon powder | 5% |
| candelilla wax | 7% |
| polyethylene wax | 10% |
| pigment D&C Yellow 6 Aluminium Lake (CI 15985) | 5% |
| pigment D&C Red 7 (CI 5850:1) | 5.8% |
| iron oxide (CI 77499) | 0.2% |
| polydimethylsiloxanol | 1% |

The pigments are milled in the fatty constituents (oils and lanolin), the other constituents are then added and the mixture is heated to 100° C.

The minute is then introduced into a twin-screw extruder and extrusion is carried out under the same conditions as in Example 1.

A lip color composition is obtained with a viscosity equal to 10 Pa.s and which has satisfactory qualities of ease of spread and softness and a certain gloss.

We claim:

1. An anhydrous composition in the form of a soft paste comprising at least one silicone gum and at least one fatty substance, said fatty substance including at least one wax, wherein said composition is prepared by a process comprising (a) mixing at least a portion of the at least one silicone gum with the at least one fatty substance including the at least one wax, heating the mixture to a temperature at which the at least one wax melts, and cooling the minute to room temperature, wherein the mixture is kneaded during at least a part of the time the composition is cooled, or (b) heating the at least one fatty substance including the at least one wax to a temperature at which the at least one wax melts, adding to the heated fatty substance the at least one silicone gum to form a mixture, and cooling the mixture to room temperature, wherein the mixture is kneaded during at least a part of the time the composition is cooled, wherein said at least one silicone gum is added to said heated fatty substance at a time either before said cooling, before and during said cooling, or during said cooling, and further wherein said composition is suitable for topical use.

2. A composition according to claim 1, wherein said silicone gum is present in an amount by weight ranging from 0.1–10% with respect to the weight of the final composition.

3. A composition according to claim 2, wherein said silicone gum is present in an amount by weight ranging from 0.1 to 3% with respect to the weight of the final composition.

4. A composition according to claim 1, wherein said silicone gum has a molecular weight of less than 1,500,000.

5. A composition according to claim 1, wherein said silicone gum is a polydimethylsiloxane, a polyphenylsiloxane, a ployhydroxysiloxane, or a gum of the formula:

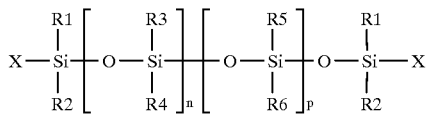

wherein:

R₁, R₂, R₅ and R₆ each independently represents an alkyl radical having from 1 to 6 carbon atoms;

R₃ and R₄ each independently represents an alkyl radical having from 1 to 6 carbon atoms or an aryl radical:

X is an alkyl radical having from 1 to 6 carbon atoms, a hydroxyl radical or a vinyl radical; and n and p are chosen so as to confer on the silicone gum a viscosity greater than 100,000 mPa.s.

6. A composition according to claim 5, wherein n and p are chosen so as to confer on the silicone gum a viscosity greater than 500,000 mPa.s.

7. A composition according to claim 5, wherein n and p have values from 0 to 5000.

8. A composition according to claim 7, wherein n and p have values from 0 to 3000.

9. A composition according to claim 1, in which at least a portion of said fatty substance is composed of at least one non-silicone fatty substance.

10. A composition according to claim 1, wherein said wax is an animal wax, a vegatable wax, a mineral wax, a synthetic wax, or a silicone wax.

11. A composition according to claim 10, wherein said animal wax is beeswax; wherein said vegatable wax is carnauba, candelilla, ouricury or japan wax, or cork fibre or sugarcane wax; wherein said mineral wax is a paraffin wax, a lignite wax, a microcrystalline wax, or an ozokerite; wherein said synthetic wax is a polyethylene wax or a wax obtained by the Fischer-Tropsch synthesis; and wherein said silicone wax is a polymethylsiloxane alkyl, alkoxy or ester wax.

12. A composition according to claim 1, wherein said wax is present in an amount by weight of from 2 to 50%, with respect to the weight of the final composition.

13. A composition according to claim 12, wherein said wax is present in an amount by weight of from 10 to 30%, with respect to the weight of the final composition.

14. A composition according to claim 1, wherein said fatty substance is a mineral oil; an animal oil; a vegatable oil; an ester of lanolic acid, of oleic acid, of lauric acid, of stearic acid or of myristic acid; an alcohol; an acetylglyceride, octanoate, decanoate or ricinoleate of an alcohol or of a polyalcohol; a hydrogenated oil which is solid at 25° C.; a mono-, di-, tri- or sucroglyceride; a lanolin; or a fatty ester which is solid at 25° C.

15. A composition according to claim 14, wherein said mineral oil is liquid paraffin or liquid petroleum; wherein said animal oil is perhydrosqualene or arara oil; wherein said vegatable oil is sweet almond, calophyllum, palm, castor, avocado, jojoba, olive or cereal germ oil; wherein said alcohol is oleyl alcohol, linoleyl alcohol, linolenyl alcohol, isostearyl alcohol or octyldodecanol; and wherein said hydrogenated oil is castor oil, palm oil, coconut oil or tallow oil.

16. A composition according to claim 1, additionally comprising at least one coulouring agent, said colouring agent being a pulverulent colouring agent, a pearlescent agent, or an organic dye.

17. A composition according to claim 16, wherein said colouring agent is present in an amount by weight up to 20% with respect to the weight of the final composition.

18. A composition according to claim 16, wherein said pulverulent colouring agent is carbon black, a chromium or iron oxide, an ultramarine, manganese pyrophosphate, iron blue, or titanium dioxide.

19. A composition according to claim 1, additionally comprising at least one pulverulent inorganic or organic filler.

20. A composition according to claim 19, wherein said filler is present in an amount by weight up to 40% with respect to the weight of the final composition.

21. A composition according to claim 20, wherein said filler is talc, mica, kaolin, zinc or titanium oxide, calcium or magnesium carbonate, silica, spherical titanium dioxide, glass or ceramic beads, a metal soap derived from carboxylic acids having 8–22 carbon atoms, a non-expanded synthetic polymer powder, an expanded powder or a powder from natural organic compounds which may or may not be crosslinked.

22. A composition according to claim 21, wherein said powder is from cereal starches.

23. A composition according to claim 2, wherein said silicone gum is present in an amount by weight ranging from 0.1 to 5% with respect to the weight of the final composition.

24. A process for preparing a cosmetic composition comprising the steps of:

(A) mixing at least one fatty substance, said fatty substance including at least one wax, with at least a portion of components, other than said at least one wax, for said cosmetic composition, said portion optionally including at least one silicone gum;

(B) heating said minute to a temperature at which the was melts;

(C) if only a portion of said other components of said composition were mixed in step (A), adding to said mixture after said melting temperature of said wax is obtained but entirely before said cooling step (D), before and during said cooling step (D), or entirely during said cooling step (D), the remainder of said other components, including, if either no silicone gum was added in step (A), or only a portion of the silicone gum was added in step (A), at least one silicone gum to form a mixture containing all components of said cosmetic composition;

(D) thereafter cooling said mixture; and (E) kneading said mixture during at least a part of said cooling step;

whereby a composition is obtained comprising at least one silicone gum and at least one fatty substance, said fatty substance including at least one wax, and further wherein said composition is anhydrous and in the form of a soft paste.

25. A process according to claim 24, wherein said kneading step is carried out in at least one extruder.

26. A process according to claim 25, wherein said mixing, heating, cooling, and kneading steps are carried out in a single twin-screw extruder.

27. A method for making up or treating the skin or lips, said method comprising applying to said skin or lips the anhydrous composition according to claim 1 in an effective amount to achieve said make-up or treatment.

* * * * *

UNITED STATES PATENT AND TRADEMARK OFFICE
CERTIFICATE OF CORRECTION

PATENT NO.: 5,948,395

DATED: September 7, 1999

INVENTORS: Véronique LE BRAS-ROULIER et al.

It is certified that an error appears in the above-identified patent and that said Letters Patent is hereby corrected as shown below:

Claim 5, col. 7, line 23, "claim 1" should read --claim 4--.

Claim 15, col. 8, line 13, "petroleum" should read --petrolatum--.

Claim 24, col. 8, line 58, "minute" should read --mixture--, and "was" should read --wax--.

Signed and Sealed this

Ninth Day of May, 2000

*Attest:*

Q. TODD DICKINSON

*Attesting Officer*     *Director of Patents and Trademarks*